(12) United States Patent
Bulgarelli et al.

(10) Patent No.: US 11,622,928 B2
(45) Date of Patent: Apr. 11, 2023

(54) ORGANIC COMPOUNDS

(71) Applicant: GIVAUDAN SA, Vernier (CH)

(72) Inventors: Nelly Bulgarelli, Loveland, OH (US); Ian Michael Harrison, Poissy (FR)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 16/971,758

(22) PCT Filed: Mar. 7, 2019

(86) PCT No.: PCT/EP2019/055722
§ 371 (c)(1),
(2) Date: Aug. 21, 2020

(87) PCT Pub. No.: WO2019/175017
PCT Pub. Date: Sep. 19, 2019

(65) Prior Publication Data
US 2021/0085590 A1    Mar. 25, 2021

(30) Foreign Application Priority Data

Mar. 13, 2018 (GB) .................................... 1804011

(51) Int. Cl.
| | | |
|---|---|---|
| *A61K 8/73* | (2006.01) |
| *A61K 8/02* | (2006.01) |
| *A61K 8/11* | (2006.01) |
| *A61K 8/19* | (2006.01) |
| *A61K 8/34* | (2006.01) |
| *A61K 8/36* | (2006.01) |
| *A61K 8/41* | (2006.01) |
| *A61K 8/44* | (2006.01) |
| *A61K 8/46* | (2006.01) |
| *A61K 8/49* | (2006.01) |
| *A61K 8/81* | (2006.01) |
| *A61K 8/84* | (2006.01) |
| *A61K 8/88* | (2006.01) |
| *A61K 8/892* | (2006.01) |
| *A61Q 5/02* | (2006.01) |
| *A61Q 5/12* | (2006.01) |
| *A61Q 19/10* | (2006.01) |

(52) U.S. Cl.
CPC ............ *A61K 8/732* (2013.01); *A61K 8/0279* (2013.01); *A61K 8/11* (2013.01); *A61K 8/19* (2013.01); *A61K 8/345* (2013.01); *A61K 8/347* (2013.01); *A61K 8/36* (2013.01); *A61K 8/361* (2013.01); *A61K 8/416* (2013.01); *A61K 8/44* (2013.01); *A61K 8/463* (2013.01); *A61K 8/4946* (2013.01); *A61K 8/73* (2013.01); *A61K 8/731* (2013.01); *A61K 8/737* (2013.01); *A61K 8/8147* (2013.01); *A61K 8/84* (2013.01); *A61K 8/88* (2013.01); *A61K 8/892* (2013.01); *A61Q 5/02* (2013.01); *A61Q 5/12* (2013.01); *A61Q 19/10* (2013.01); *A61K 2800/624* (2013.01)

(58) Field of Classification Search
CPC .......... A61K 8/19; A61K 8/347; A61K 8/463; A61K 8/416; A61K 8/892; A61K 8/0279; A61K 8/44; A61K 8/4946; A61K 8/11; A61K 8/36; A61K 8/8147; A61K 8/84; A61K 8/345; A61K 8/737; A61K 8/88; A61K 8/361; A61K 8/732; A61K 8/73; A61K 8/731; A61K 2800/624; A61K 2800/544; A61Q 5/12; A61Q 5/02; A61Q 5/00; A61Q 19/10; A61Q 19/00
See application file for complete search history.

(56) References Cited

U.S. PATENT DOCUMENTS

| | | |
|---|---|---|
| 5,607,678 A | 3/1997 | Moore et al. |
| 8,927,026 B2 | 1/2015 | Dihora et al. |
| 2003/0050200 A1 | 3/2003 | Chen |
| 2004/0071746 A1* | 4/2004 | Popplewell ............... A61K 8/84 424/401 |
| 2005/0003975 A1* | 1/2005 | Browne ................ C11D 17/006 510/101 |
| 2008/0274149 A1 | 11/2008 | Seiler et al. |
| 2011/0245141 A1* | 10/2011 | Gizaw ................ C11D 17/0039 510/516 |
| 2012/0263668 A1 | 10/2012 | Cowan et al. |
| 2012/0276210 A1 | 11/2012 | Dihora et al. |
| 2012/0282309 A1 | 11/2012 | Dihora et al. |
| 2017/0175052 A1* | 6/2017 | Howard ................. C11D 3/222 |
| 2017/0191000 A1 | 7/2017 | Cetti et al. |

FOREIGN PATENT DOCUMENTS

| | | |
|---|---|---|
| CA | 2812137 A1 | 4/2012 |
| EP | 0191564 A2 | 8/1986 |
| GB | 2546419 A | 7/2017 |

(Continued)

OTHER PUBLICATIONS

Li, Jason. Starch Applications for Delivery Systems, 2013, pp. 195-210. (Year: 2013).*

(Continued)

*Primary Examiner* — Doan T Phan
(74) *Attorney, Agent, or Firm* — Norris McLaughlin PA

(57) ABSTRACT

Disclosed is a composition comprising at least one core-shell microcapsule in a suspending medium. The microcapsule comprises a core and a shell around said core. The shell comprises a hyperbranched polysaccharide selected from the group consisting of amylopectins, dextrins, hyperbranched starches, glycogen and phytoglycogen and mixtures thereof.

16 Claims, 1 Drawing Sheet

(56) References Cited

FOREIGN PATENT DOCUMENTS

| GB | 2546519 A | 7/2017 |
|---|---|---|
| WO | 9723194 A1 | 7/1997 |
| WO | 2007137441 A1 | 12/2007 |
| WO | 2016183209 A1 | 11/2016 |

OTHER PUBLICATIONS

International Search Report and Written Opinion of the International Searching Authority for corresponding application PCT/EP2019/055722 dated Jun. 26, 2019.

GB Search Report for corresponding application GB 1804011.3 dated Oct. 15, 2018.

Y. Zhou, et al: "Self-Assembly of Hyperbranched Polymers and Its Biomedical Applications"; Adv. Mater 201, 22, p. 4567-4590; © 2010 Wiley-VCH Verlag GmbH & Co. KGaA, Weinheim; wileyonlinelibrary.com.

A. A. Albalasmeh, et al: "A new method for rapid determination of carbohydrate and total carbon concentrations using UV spectrophotometry"; Carbohydrate Polymers 97 (2013); p. 253-261; © 2013 Elsevier Ltd.

Y. Takeda, et al: "Branching of amylose by the branching isoenzymes of maize endosperm"; Carbohydrate Research, 240 (1993); p. 253-263; Elsevier Science Publishers B.V., Amsterdam.

M. Dubois, et al: "Colorimetric Method for Determination of Sugars and Related Substances"; Analytical Chemistry, vol. 28, No. 3, Mar. 1956, p. 350-356.

Luz, P. P. et al., "Dextrin-Microencapsulated Porphyrin: Luminescent Properties", Annals of the New York Academy of Sciences, Jun. 28, 2008, vol. 1130, No. 1, pp. 91-96.

* cited by examiner

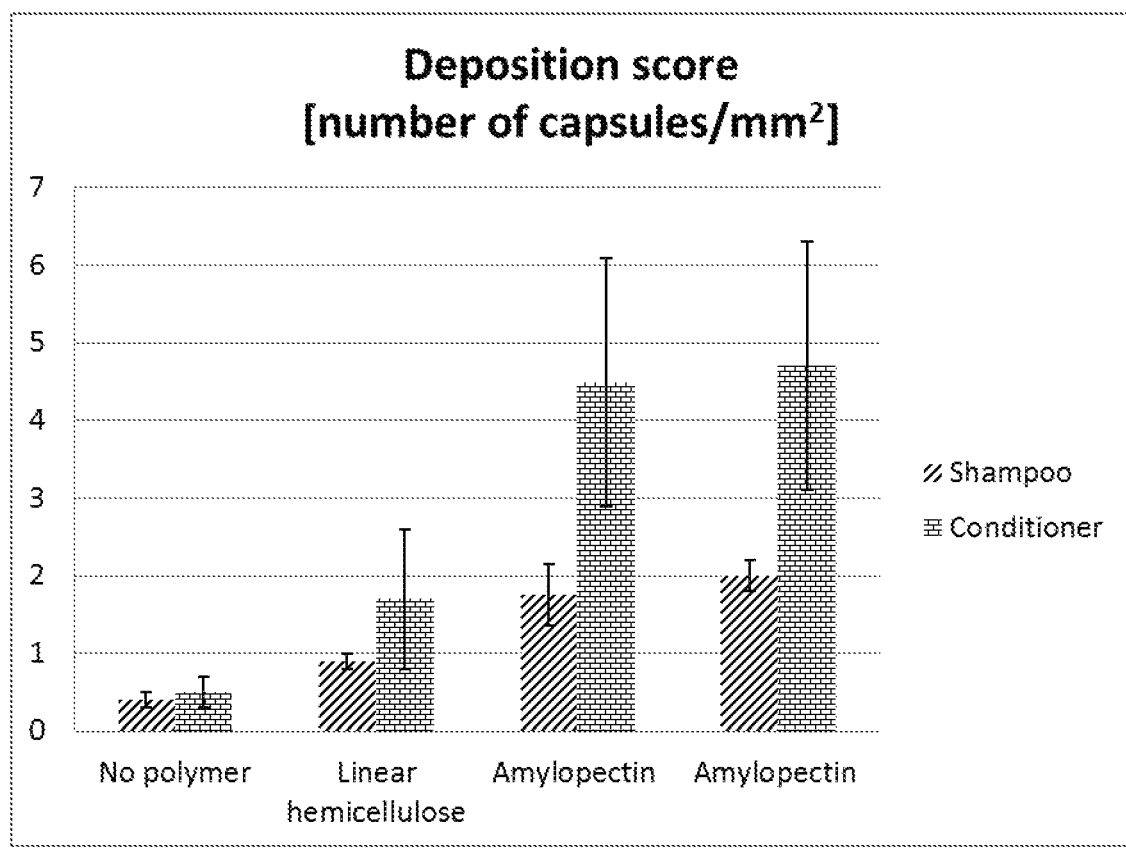

ORGANIC COMPOUNDS

This is an application filed under 35 USC 371 based on PCT/EP2019/055722, filed 7 Mar. 2019, which in turn is based on GB 1804011.3 filed 13 Mar. 2018. The present application claims the full priority benefit of these prior applications and herein incorporates by reference the full disclosures of these prior applications.

The present invention relates to core-shell microcapsules showing improved deposition on keratinous substrates and improved rinse resistance once deposited on these substrates.

It is known to incorporate encapsulated functional materials in consumer products, such as household care, personal care, and fabric care products. Functional materials include for example fragrances, cosmetic agents, drugs, and substrate enhancers.

Microcapsules that are particularly suitable for delivery such functional materials are core-shell microcapsules, wherein the core usually comprises the functional materials and the shell is impervious or partially impervious to the functional material. Usually these microcapsules are used in aqueous media and the encapsulated ingredients are hydrophobic. A broad selection of shell materials can be used, provided this shell material is impervious or partially impervious to the encapsulated ingredient.

Among the functional materials, fragrance compositions are encapsulated for a variety of reasons. Microcapsules can isolate and protect perfume ingredients from external suspending media, such as consumer product bases, in which they may be incompatible or unstable. They are also used to assist in the deposition of perfume ingredients onto substrates, such as skin, hair, fabrics or hard household surfaces. They can also act as a means of controlling the spatio-temporal release of perfume.

Thermosetting resins are common encapsulating materials for perfume compositions. Core-shell microcapsules formed from aminoplast resins, polyurea resins, polyurethane resins, polyacrylate resin, and combinations thereof are generally quite resistant to fragrance leakage when dispersed in aqueous suspending media, even in surfactant-containing media.

Furthermore, when incorporated into consumer products, such as laundry detergents or conditioners, they provide perfumery benefits that are unattainable if perfume is incorporated directly into those products.

In many instances, however, the deposition and adherence of these microcapsules on smooth surfaces and especially on keratinous surfaces, such as skin and hair, are insufficient and the expected benefits associated with the use of microcapsules are not optimal. This is especially the case for rinse-off products involving large amounts of water. In this case, a lack of deposition may be due to the dilution of the microcapsules to a such a low level that the probability for a microcapsule to find the surface on which it is intended to deposit. Large volumes of rinse water may also wash off the microcapsules from the surface.

US 2012/0282309 A1 discloses a hair conditioner composition containing anionic polyacrylate microcapsules and a deposition aid, such as a cationic deposition polymer or an aminosilicone. U.S. Pat. No. 8,927,026 B2 relates to a shampoo composition containing anionic polyacrylate microcapsules and a cationic deposition polymer.

In both of these cases, the microcapsules are coated with an anionic surfactant and the cationic polymer is added by forming a premix with the coated microcapsules before being added to the shampoo or conditioner base. Such an approach is complex and may lead to electrostatically induced incompatibility issues, such as aggregation of the microcapsules in the premix and phase segragation during admixing both premix and shampoo or conditioner base. This may affect the properties of the end product and may require modifying the composition of the end product in which the microcapsules are used.

It is therefore a problem underlying the present invention to overcome the above-mentioned shortcomings in the prior art. In particular, it is a problem underlying the present invention to provide microcapsules showing improved deposition on keratinous substrates and improved rinse resistance once deposited on these substrates. The microcapsules should be inexpensive and simple in manufacture and versatile with respect to their application. No or only minimal modification of the product composition should be required in connection with their use.

In a first aspect of the present invention, there is provided a composition comprising at least one core-shell microcapsule in a suspending medium. Said microcapsule comprises a core and a shell around said core. The shell comprises a hyperbranched polysaccharide selected from the group consisting of amylopectins, dextrins, hyperbranched starches, glycogen and phytoglycogen, and mixtures thereof.

In the context of the present invention, the term "hyperbranched polysaccharide", or more generally "hyperbranched polymer", refers to a polymer comprising a primary chain or a nucleus, one or more secondary chains attached to the primary chain or the nucleus and one or more tertiary chains attached to at least one of said secondary chains.

Typically, a secondary chain has one or more tertiary chains attached to it, but—in order to avoid any ambiguity—some secondary chains in the hyperbranched polymer may also have no tertiary chain attached to it. Preferably, at least 10%, preferably more than 20%, even more preferably more than 25%, of the secondary chains in the hyperbranched polymer have one or more tertiary chains attached to it.

The invention is based on the discovery that embedding and/or attaching a hyperbranched polysaccharide into and/or onto core-shell microcapsules improves both the deposition and rinse-resistance of core-shell microcapsules, in particular on keratinous surfaces such as skin or hair.

In particular, the improved deposition and rinse-resistance are observed when core-shell microcapsules are applied to skin or hair by means of rinse-off consumer products, such as shampoos, shower gels, soaps and detergents and conditionning compositions, for example fabric care conditioners or hair care conditioners.

This finding was surprising as it is known that surfaces treated with hyperbranched polyglycerols are known to be resistant to cells and protein adhesion, providing good protection against biofilm formation, see for example Y. Zhou et al., Adv. Mater. 2010, 22, 4567-4590.

A suitable way to characterize the extent of branching of above hyperbranched polysaccharides is to refer to their 1,6'-glycosicid bond to 1,4'-glycosidic bond ratios.

In a specific embodiment of the invention, the the ratio of 1,6'-glycosidic bonds to 1,4'-glycosidic bonds in the hyperbranched polysaccaride is greater than 1/50, more particularly greater than 1/40 and still more particularly greater than 1/35. Hyperbranched polysaccarides having 1,6'-glycosidic bond to 1,4'-glycosidic bond ratio smaller than 1/50 have properties that are similar to those of linear polysaccharides and are therefore less suitable for the sake of the present invention. In particular, the viscosity of microcapsule slurries with linear polysaccharides increases strongly with decreasing 1,6'-glycosidic to 1,4'-glycosidic bond ratio at constant polysaccharide molecular weight, making the slurry less flowable and more difficult to incorporate into the end product.

In the context of the present invention, hyperbranced polymer can be embedded in and/or attached to the microcapsule shell. The amount of hyperbranced polymer, in particular embedded in and/or attached to the microcapsule shell, can be from 0.01 to 1 wt %, more particularly from 0.02 to 0.5 wt % and still more particularly from 0.05 to 0.25 wt %, referred to the total weight of the microcapsule suspension. At lower amounts, the hyperbranched polymer is ineffective, while, at higher amounts the surface of the microcapsules is saturated and no more hyperbranched polymer may be incorporated into it. This may result in undesired effects, such as an increase of the viscosity of the microcapsule slurry or a phase separation in the slurry.

The core can comprise a fragrance ingredient, a cosmetic ingredient or a mixture thereof.

In advantageous embodiments of the invention, the shell of the at least one core-shell microcapsule comprises a thermosetting resin, in particular a thermosetting resin selected from the group consisting of aminoplast resins, polyurea resins, polyacrylic resins, and mixtures thereof. These resins are well known to the art to be particularly suitable for the encapsulation of small and/or volatile functional materials.

In a second aspect of the invention, there is provided a method for embedding and/or attaching hyperbranched polymers into and/or onto microcapsule shells, comprising the steps of:
- dispersing droplets of a core material in a suspending medium, in particular comprising an emulsifier, in the presence of shell-forming monomers, pre-polymers or pre-condensates to obtain an emulsion, in particular an oil-in-water emulsion;
- causing the monomers, pre-polymers or pre-condensates to react at the interface of the droplets and the suspending medium to obtain a slurry of core-shell microcapsules;
- adding a hyperbranched polymer;
- obtaining a composition comprising a slurry of core-shell microcapsules, wherein the hyperbranched polymer is embedded into and/or attached into and/or onto the shells of the core-shell microcapsules;
- optionally adding to the slurry one more of a suspending agent or preservative;
- optionally dehydrating the slurry to form a composition of core-shell microcapsules, in particular in powder form.

Notably, addition of hyperbranched polymer may be effected before the shell-forming monomer, pre-polymers or pre-condensates are caused to react, during the reaction of these materials or after completion of the reaction. The entire amount of hyperbranched polymer may be added in one operation, or it can be added sequentially and/or portionwise.

In specific embodiments of the invention, the hyperbranched polymer is selected from a group consisting of hyperbranched polyglycerols, hyperbranched polyerythritols and hyperbranched polysaccharides. These hyperbranched polymers have the advantage of being widely spread in nature and/or non toxic, as well as fully biodegradable.

In further specific embodiments of the invention, the hyperbranched polysaccharide is selected from a group consisting of amylopectins, dextrins, hyperbranched starches, glycogen and phytoglycogen and mixtures thereof. These polymers have the advantage of being readily available commercially.

Furthermore, the present invention refers to a microcapsule, in particular a core-shell microcapsule, obtainalbe by the above-stated method. The present invention also refers to a composition comprising at least one such microcapsule in a suspending medium.

In a third aspect of the invention, there is provided a method of enhancing deposition of at least one core-shell microcapsule on a surface, in particular a keratinous surface, the method comprising the step of embedding and/or attaching a hyperbranched polymer into and/or onto the shell of said core-shell microcapsule. Advantagously, this is achieved by a method for embedding and/or attaching hyperbranched polymers into and/or onto microcapsule shells as stated above. The invention also refers to the use of a hyperbranched polymer for enhancing the deposition of at least one core-shell microcapsule on a surface, in particular a keratinous surface, by embedding and/or attaching the hyperbranched polymer into and/or onto the shell of said core-shell microcapsule, in particular by the above method.

In a fourth aspect of the invention, there is provided a method of increasing the rinse-resistance of the at least one core-shell microcapsule deposited on a surface, in particular on a keratinous surface, the method comprising the step of embedding and/or attaching a hyperbranched polymer into and/or onto the shell of the core-shell microcapsule. Advantagously, this is achieved by a method for embedding and/or attaching hyperbranched polymers into and/or onto microcapsule shells as stated above. The invention also refers to the use of a hyperbranched polymer for increasing the rinse-resistance of at least one core-shell microcapsule deposited on a surface, in particular on a keratinous surface, by of embedding and/or attaching a hyperbranched polymer into and/or onto the shell of the core-shell microcapsule, in particular by the above method.

Furthermore the present invention refers to a consumer product comprising a composition as described hereinabove. The comsumer product can be a shampoo, a hair care conditioner, a shower gel or a liquid soap.

If the hyperbranched polymer is generated from a nucleus, the nucleus can have two or more chemical functions on which a secondary chain may be attached. In the following, this shall be referred to as a polyfunctional nucleus. The secondary chain may grow from a nucleus chemical function by polymerization or may be attached to a nucleus chemical function by grafting. The polyfunctional nucleus may include, glycerol, erythritol, glycidol, 2,2-bismethylol-proionic acid, 3-hydroxy-2-(hydroxymethyl)-2-methylpropanoic acid, ethylene glycol di(meth)acrylate, triethylene glycol tri(meth)acrylate, pentaerythritol triacrylate, a furanose (such as fructose), 1,2-di(oxiran-2-yl)ethane-1,2-diol, or a pyranose (such as glucose).

In a preferred embodiment of the present invention, the polyfunctional nucleus is selected from the group consisting of, glycerol, erythritol, glycidol, furanose, pyranose, and glycogenin.

In a particular embodiment, the hyperbranched polymer comprises secondary tertiary chains, and higher order chains, wherein the secondary chains are attached to a primary chain or a nucleus.

The primary, secondary, tertiary and higher order chains may be any polyfunctional polymer, having one or more functional group, preferably a plurality of functional groups, such as hydroxy, amine, glycidyl, isocyanate, vinyl and (meth)acryloyl.

In a preferred embodiment of the present invention, the primary, secondary, tertiary and higher order chains have a plurality of hydroxy groups and are selected from the group consisting of polyglycerol, polyerithrytol and polysaccharides.

The polysaccharide chains may comprise various sugar moieties and moieties derived from sugars. Sugar moieties may include pyranoses and furanoses, such as glucose, rhamnose, xylose, arabinose, galactose, fucose, apiose and fructose. Moieties derived from sugars may include dehydrated pyranoses, dehydrated furanoses, glucuronic acid, mannuronic acid, glucosamine and sulfato-galactose. A chain may comprise different sugar moieties and moieties derived from sugars.

In an embodiment the polysaccharide chains comprise pyranose monomers, such as glucose.

In a particular embodiment, the pyranose monomer is glucose. Typically, the covalent bonds between two glucose rings in a polysaccharide chain is formed between the hydroxyl group on carbon C1 of one of the ring and the hydroxyl group of carbon C4' of the other ring (so called 1,4' glycosidic bond), yielding starch-based polymers if $\alpha$-D-glucose is involved or cellulose-based polymers if R-D-glucose is involved.

On the other hand, branching on a polysaccharide chain usually involves the hydroxyl group located on carbon C1 of any of the rings located on the first chain and a hydroxyl group located on carbon C6', carbon C3' or carbon C2' of any ring located on the second chain, yielding so-called 1,6'-glucosidic bond, 1,3'-glucosidic bond or 1,2'-glucosidic bond.

Particularly preferred hyperbranched polysaccharides include those natural polysaccharides which may be selected from the group consisting of amylopectins, glycogen, phytoglycogen and enzymatically branched starches. These polysaccharide polymers are characterized by the existence of chains of 1,4'-bonded pyranoses connected to each other by 1,6'-, 1,3'- and 1,2'-bonds.

Amylopectin is characterized by a tree-like dendritic arrangement of chains of $\alpha$-D-glucose units bonded to each other by 1,4'-glycosidic bonds, with a primary chain (or first order chain), secondary chains (or second-order chains), tertiary chains (or third-order chains) and higher order chains connected in such a way that each chain of order X is attached to a chain of order X-1 by its first glucose, wherein most of the bonds involved in the branching are 1,6'-glycosidic bonds. The ratio of 1,6'-glycosidic bonds to 1,4'-glycosidic bonds in amylopectin is typically between about 1/30 and about 1/24.

The number of pyranose units involved in the amylopectin moiety depends on the origin of the starch source. For example the number of linked pyranose units involved in the amylopectin moieties of maize starch is between 280 and 35,000, while the number of linked pyranose units involved in the amylopectin moieties of potato starch is between 1,100 and 220,000.

Acid or enzymatic degradation of amylopectins leads to the formation of hyperbranched dextrins. These dextrins may additionally comprise 1,2'-glycosidic bonds and 1,3'-glycosidic bonds. These dextrins are also useful for the sake of the present invention.

Glycogen and phytoglycogen are similar to amylopectin in the way the branches are connected to each other, but are characterized by a nearly spherical dendritic arrangement of the branches and by a higher branching density compared to amylopectin. The ratio of 1,6'-glycosidic bonds to 1,4'-glycosidic bonds in amylopectin is typically between 1/12 and 1/8.

Starches submitted to enzymatic treatment with a glycogen branching enzyme (Identification number: EC 2.4.1.18, also called glucuronosyltransferase) have typically 1,6'-glycosidic bonds to 1,4'-glycosidic bond ratios between 1/25 and 1/8 and therefore also suitable for the sake of the present invention. For example, hyperbranched starch is obtained by treating starch or a starch derivative in partially or completely gelatinized form with glycogen branching enzyme (Identification number: EC 2.4.1.18). The hyperbranched starch has a molecular branching degree of 6%, preferably 6.5%. The molecular branching degree is defined as percentage of $\alpha$-1,6-glycosidic linkages of the total of $\alpha$-1,6- and $\alpha$-1,4-glycosidic linkages ($\alpha$-1, 6/($\alpha$-1,6+$\alpha$- 1,4) x 100%).

The level of 1,6'-glycosidic bonds in a polysaccharide may be determined by measuring the difference in the amount of reducing ends before and after enzymatic debranching of the product using isoamylase (see for example Y. Takeda et al., Carbohydr. Res. 1993, 240, 253-263).

Hydrophobically modified amylopectin-rich starches, such as starch functionalized with octenyl succinic anhydride (OSA) or dodecenyl succinic anhydride (DDSA) are also useful for the sake of the present invention. Typically, these modified starches have substitution grade between 1 and 10% by weight of the dry starch.

Other specific hyperbranched polymers that may be useful in accordance with the present invention may be selected from the group consisting of synthetic poly(polyols), such as polyglycerols, polyerythritol, poly(3-ethyl-3-hydroxymethyloxetane) and poly(2-hydroxymethyloxetane), hyperbranched polymers, such as poyl(1,6-anhydro-β-D-gluco (manno, galacto)pyranose), poly(5,6-anhydro-1,2-O-isopropylidene-α-D-glucofuranose) hyperbranched polyether ketal glycopolymer, poly(3-hydroxy-2-(hydroxymethyl)-2-methylpropanoic acid), poly(2,2-di(oxiran-2-yl)propanoyl chloride or poly(ether-co-ester) hyperbranched polymers.

In a particular embodiment ot the present invention, core-shell microcapsules may be formed by preparing a slurry containing core-shell microcapsules, and adding a hyperbranched polymer to the slurry in order for it to adsorb onto the surface of the microcapsules.

In another particular embodiment, the hyperbranched polymer may be incorporated into core-shell microcapsules by adding the hyperbranched polymer to a slurry of nascent microcapsules and embedding and/or attaching the hyperbranched polymer into and/or onto the shells of the nascent core-shell microcapsules as they form.

In the context of the present invention, the term "nascent" as it refers to microcapsules, describes microcapsules that are in the process of being formed and where shell-forming reaction, such as interfacial polymerization, polyaddition, polycondensation, radical polymerization, ring-opening polymerization, and the like, is taking place.

In these shell-forming processes, the locus of the reaction is typically the interface separating droplets of hydrophobic core material, from an aqueous external phase in which the droplets are dispersed. In a typical microencapsulation process, this interface is stabilized by surfactants or polymeric emulsifiers.

In a particular embodiment of the present invention, the hyperbranched polymer is added during the microcapsule shell-formation process, such that the polymer becomes physically embedded into the shells as microencapsulation proceeds.

In a more particular embodiment, the composition of the present invention may be formed according to a method comprising the following steps:

a) dispersing droplets of functional material in an aqueous phase comprising an emulsifier in the presence of shell-forming monomers, pre-polymers or pre-condensates to form an oil-in-water emulsion;

b) causing the monomers, pre-polymers or pre-condensates to react at the interface of the droplets and the aqueous phase to form a slurry of nascent core-shell microcapsules;

c) adding a hyperbranched polymer to the slurry of nascent core-shell microcapsules to form a composition comprising a slurry of core-shell microcapsules, wherein the hyperbranched polymer is embedded into the shells of the core-shell microcapsules;

d) optionally adding to the slurry one more of a suspending agent, a preservative or any other conventional excipients;

e) optionally dehydrating the slurry to form a composition of core-shell microcapsules in powder form.

In carrying out step a) the mixing apparatus and speed of mixing may be controlled in a manner known per se, in order to provide any desired droplet size. Mixing may be effected with a propeller, a turbine, a cross-beam stirrer with pitched bean, such as Mig stirrer. Typically, the emulsion is formed at a stirring speed within an interval of 100 to 2000 rpm, more particularly from 250 to 1500 rpm, and still more particularly from 500 rpm to 1000 rpm for a vessel having a volume of 1 litre, equipped with a cross-beam stirrer with pitched bean, and having a stirrer diameter to reactor diameter ratio of 0.7. The stirrer apparatus may comprise a turbine, a Mig stirrer. The person skilled in the art will however understand that such stirring conditions may change depending on the size of the reactor and of the volume of the slurry, on the exact geometry of the stirrer on the ratio of the diameter of the stirrer to the diameter of the reactor diameter ratios. For example, for a Mig stirrer with stirrer to reactor diameter ratio from 0.5 to 0.9 and slurry volumes ranging from 0.5 to 8 tons, the preferable agitation speed in the context of the present invention is from 150 rpm to 50 rpm.

In carrying out step c) the addition of hyperbranched polymer may be made before the shell-forming monomer, pre-polymers or pre-condensates are caused to react, or during the reaction of these materials. The entire amount of hyperbranched polymer may be added in one operation, or it can be added sequentially and/or portionwise.

A broad selection of functional materials may be employed in core-shell microcapsules of the present invention. The core may in particular comprise a hydrophobic material selected from the group consisting of oils, essential oils, fragrance oils, biocides, pheromones, lipophilic cosmetic ingredients and topical drugs.

In one embodiment, the hydrophobic core material is a fragrance composition comprising at least one fragrance ingredient.

A comprehensive list of perfume ingredients that may be encapsulated in accordance with the present invention may be found in the perfumery literature, for example "*Perfume & Flavor Chemicals*", S. Arctander (Allured Publishing, 1994). Encapsulated perfume according to the present invention comprise preferably perfume ingredients selected from ADOXAL™ (2,6,10-trimethylundec-9-enal); AGRUMEX™ (2-(tert-butyl)cyclohexyl acetate); ALDEHYDE C 10 DECYLIC (decanal); ALDEHYDE C 11 MOA (2-methyldecana); ALDEHYDE C 11 UNDECYLENIC (undec-10-enal); ALDEHYDE C 110 UNDECYLIC (undecanal); ALDEHYDE C 12 LAURIC (dodecanal); ALDEHYDE C 12 MNA PURE (2-methylundecanal); ALDEHYDE ISO C 11 ((E)-undec-9-enal); ALDEHYDE MANDARINE 10%/TEC ((E)-dodec-2-enal); ALLYL AMYL GLYCOLATE (allyl 2-(isopentyloxy)acetate); ALLYL CYCLOHEXYL PROPIONATE (allyl 3-cyclohexylpropanoate); ALLYL OENANTHATE (allyl heptanoate); AMBER CORE™ (1-((2-(tert-butyl)cyclohexyl)oxy)butan-2-ol); AMBERMAX™ (1,3,4,5,6,7-hexahydro-.beta.,1,1,5,5-pentamethyl-2H-2,4a-methanonaphthal-ene-8-ethanol); AMYL SALICYLATE (pentyl 2-hydroxybenzoate); APHERMATE (1-(3,3-dimethylcyclohexyl)ethyl formate); BELAMBRE™ ((1R,2S,4R)-2'-isopropyl-1,7,7-trimethylspiro[bicyclo[2.2.1]heptane-2,4'-[1,3]dioxane]); BIGARYL (8-(sec-butyl)-5,6,7,8-tetrahydroquinoline); BOISAMBRENE™ FORTE™ ((ethoxymethoxy)cyclododecane); BOISIRIS™ ((1S,2R,5R)-2-ethoxy-2,6,6-trimethyl-9-methylenebicyclo[3.3.1]nonane); BORNYL ACETATE ((2S,4S)-1,7,7-trimethylbicyclo[2.2.1]heptan-2-yl acetate); BUTYL BUTYRO LACTATE (1-butoxy-1-oxopropan-2-yl butyrate); BUTYL CYCLOHEXYL ACETATE PARA (4-(tert-butyl)cyclohexyl acetate); CARYOPHYLLENE ((Z)-4,11,11-trimethyl-8-methylenebicyclo[7.2.0]undec-4-ene); CASHMERAN™ (1,1,2,3,3-pentamethyl-2,3,6,7-tetrahydro-1H-inden-4(5H)-one); CASSYRANE™ (5-tert-butyl-2-methyl-5-propyl-2H-furan); CITRAL ((E)-3,7-dimethylocta-2,6-dienal); CITRAL LEMAROME™ N ((E)-3,7-dimethylocta-2,6-dienal); CITRATHAL™ R ((Z)-1,1-diethoxy-3,7-dimethylocta-2,6-diene); CITRONELLAL (3,7-dimethyloct-6-enal); CITRONELLOL (3,7-dimethyloct-6-en-1-ol); CITRONELLYL ACETATE (3,7-dimethyloct-6-en-1-yl acetate); CITRONELLYL FORMATE (3,7-dimethyloct-6-en-1-yl formate); CITRONELLYL NITRILE (3,7-dimethyloct-6-enenitrile); CITRONELLYL PROPIONATE (3,7-dimethyloct-6-en-1-yl propionate); CLONAL (dodecanenitrile); CORANOL (4-cyclohexyl-2-methylbutan-2-ol); COSMONE™ ((Z)-3-methylcyclotetradec-5-enone); CYCLAMEN ALDEHYDE (3-(4-isopropylphenyl)-2-methylpropanal); CYCLOGALBANATE (allyl 2-(cyclohexyloxy)acetate); CYCLOHEXYL SALICYLATE (cyclohexyl 2-hydroxybenzoate); CYCLOMYRAL (8,8-dimethyl-1,2,3,4,5,6,7,8-octahydronaphthalene-2-carbaldehyde); DAMASCENONE ((E)-1-(2,6,6-trimethylcyclohexa-1,3-dien-1-yl)but-2-en-1-one); DAMASCONE ALPHA ((E)-1-(2,6,6-trimethylcyclohex-2-en-1-yl)but-2-en-1-one); DAMASCONE DELTA ((E)-1-(2,6,6-trimethylcyclohex-3-en-1-yl)but-2-en-1-one); DECENAL-4-TRANS ((E)-dec-4-enal); DELPHONE (2-pentylcyclopentanone); DIHYDRO ANETHOLE (propanedioic acid 1-(1-(3,3-dimethylcyclohexyl)ethyl) 3-ethyl ester); DIHYDRO JASMONE (3-methyl-2-pentylcyclopent-2-enone); DIMETHYL BENZYL CARBINOL (2-methyl-1-phenylpropan-2-ol); DIMETHYL BENZYL CARBINYL ACETATE (2-methyl-1-phenylpropan-2-yl acetate); DIMETHYL BENZYL CARBINYL BUTYRATE (2-methyl-1-phenylpropan-2-yl butyrate); DIMETHYL OCTENONE (4,7-dimethyloct-6-en-3-one); DIMETOL (2,6-dimethylheptan-2-ol); DIPENTENE (1-methyl-4-(prop-1-en-2-yl)cyclohex-1-ene); DUPICAL™ ((E)-4-((3aS,7aS)-hexahydro-1H-4,7-methanoinden-5(6H)-ylidene)butanal); EBANOL™ ((E)-3-methyl-5-(2,2,3-trimethylcyclopent-3-en-1-yl)pent-4-en-2-ol); ETHYL CAPROATE (ethyl hexanoate); ETHYL CAPRYLATE (ethyl octanoate); ETHYL LINALOOL ((E)-

3,7-dimethylnona-1,6-dien-3-ol); ETHYL LINALYL ACETATE ((Z)-3,7-dimethylnona-1,6-dien-3-yl acetate); ETHYL OENANTHATE (ethyl heptanoate); ETHYL SAFRANATE (ethyl 2,6,6-trimethylcyclohexa-1,3-diene-1-carboxylate); EUCALYPTOL ((1s,4s)-1,3,3-trimethyl-2-oxabicyclo[2.2.2]octane); FENCHYL ACETATE ((2S)-1,3,3-trimethylbicyclo[2.2.1]heptan-2-yl acetate); FENCHYL ALCOHOL ((1S,2R,4R)-1,3,3-trimethylbicyclo[2.2.1]heptan-2-ol); FIXOLIDE™ (1-(3,5,5,6,8,8-hexamethyl-5,6,7,8-tetrahydronaphthalen-2-yl)ethanone); FLORALOZONE™ (3-(4-ethylphenyl)-2,2-dimethylpropanal); FLORHYDRAL (3-(3-isopropylphenyl)butanal); FLOROCYCLENE™ ((3aR,6S,7aS)-3a,4,5,6,7,7a-hexahydro-1H-4,7-methanoinden-6-yl propionate); FLOROPAL™ (2,4,6-trimethyl-4-phenyl-1,3-dioxane); FRESKOMENTHE™ (2-(sec-butyl) cyclohexanone); FRUITATE ((3aS,4S,7R,7aS)-ethyl octahydro-1H-4,7-methanoindene-3a-carboxylate); FRUTONILE (2-methyldecanenitrile); GALBANONE™ PURE (1-(3,3-dimethylcyclohex-1-en-1-yl)pent-4-en-1-one); GARDOCYCLENE™ ((3aR,6S,7aS)-3a,4,5,6,7,7a-hexahydro-1H-4,7-methanoinden-6-yl isobutyrate); GERANIOL ((E)-3,7-dimethylocta-2,6-dien-1-ol); GERANYL ACETATE SYNTHETIC ((E)-3,7-dimethylocta-2,6-dien-1-yl acetate); GERANYL ISOBUTYRATE ((E)-3,7-dimethylocta-2,6-dien-1-yl isobutyrate); GIVESCONE™ (ethyl 2-ethyl-6,6-dimethylcyclohex-2-enecarboxylate); HABANOLIDE™ ((E)-oxacyclohexadec-12-en-2-one); HEDIONE™ (methyl 3-oxo-2-pentylcyclopentaneacetate); HERBANATE™ ((2S)-ethyl 3-isopropylbicyclo[2.2.1]hept-5-ene-2-carboxylate); HEXENYL-3-CIS BUTYRATE ((Z)-hex-3-en-1-yl butyrate); HEXYL CINNAMIC ALDEHYDE ((E)-2-benzylideneoctanal); HEXYL ISOBUTYRATE (hexyl isobutyrate); HEXYL SALICYLATE (hexyl 2-hydroxybenzoate); INDOFLOR™ (4,4a,5,9b-tetrahydroindeno[1,2-d][1,3]dioxine); IONONE BETA ((E)-4-(2,6,6-trimethylcyclohex-1-en-1-yl)but-3-en-2-one); IRISONE ALPHA ((E)-4-(2,6,6-trimethylcyclohex-2-en-1-yl)but-3-en-2-one); IRONE ALPHA ((E)-4-(2,5,6,6-tetramethylcyclohex-2-en-1-yl)but-3-en-2-one); ISO E SUPER™ (1-(2,3,8,8-tetramethyl-1,2,3,4,5,6,7,8-octahydronaphthalen-2-yl) ethanone); ISOCYCLOCITRAL (2,4,6-trimethylcyclohex-3-enecarbaldehyde); ISONONYL ACETATE (3,5,5-trimethylhexyl acetate); ISOPROPYL METHYL-2-BUTYRATE (isopropyl 2-methyl butanoate); ISORALDEINE™ 70 ((E)-3-methyl-4-(2,6,6-trimethylcyclohex-2-en-1-yl)but-3-en-2-one); JASMACYCLENE™ ((3aR,6S,7aS)-3a,4,5,6,7,7a-hexahydro-1H-4,7-methanoinden-6-yl acetate); JASMONE CIS ((Z)-3-methyl-2-(pent-2-en-1-yl)cyclopent-2-enone); KARANAL™ (5-(sec-butyl)-2-(2,4-dimethylcyclohex-3-en-1-yl)-5-methyl-1,3-dioxane); KOAVONE ((Z)-3,4,5,6,6-pentamethylhept-3-en-2-one); LEAF ACETAL ((Z)-1-(1-ethoxyethoxy)hex-3-ene); LEMONILE™ ((2E,6Z)-3,7-dimethylnona-2,6-dienenitrile); LIFFAROME™ GIV ((Z)-hex-3-en-1-yl methyl carbonate); LILIAL™ (3-(4-(tert-butyl)phenyl)-2-methylpropanal); LINALOOL (3,7-dimethylocta-1,6-dien-3-ol); LINALYL ACETATE (3,7-dimethylocta-1,6-dien-3-yl acetate); MAHONIAL™ ((4E)-9-hydroxy-5,9-dimethyl-4-decenal); MALTYL ISOBUTYRATE (2-methyl-4-oxo-4H-pyran-3-yl isobutyrate); MANZANATE (ethyl 2-methylpentanoate); MELONAL™ (2,6-dimethylhept-5-enal); MENTHOL (2-isopropyl-5-methylcyclohexanol); MENTHONE (2-isopropyl-5-methylcyclohexanone); METHYL CEDRYL KETONE (1-((1S,8aS)-1,4,4,6-tetramethyl-2,3,3a,4,5,8-hexahydro-1H-5,8a-methanoazuen-7-yl)ethanone); METHYL NONYL KETONE EXTRA (undecan-2-one); METHYL OCTYNE CARBONATE (methyl non-2-ynoate); METHYL PAMPLEMOUSSE (6,6-dimethoxy-2,5,5-trimethylhex-2-ene); MYRALDENE (4-(4-methylpent-3-en-1-yl)cyclohex-3-enecarbaldehyde); NECTARYL (2-(2-(4-methylcyclohex-3-en-1-yl)propyl)cyclopentanone); NEOBERGAMATE™ FORTE (2-methyl-6-methyleneoct-7-en-2-yl acetate); NEOFOLIONE™ ((E)-methyl non-2-enoate); NEROLIDYLE™ ((Z)-3,7,11-trimethyldodeca-1,6,10-trien-3-yl acetate); NERYL ACETATE HC ((Z)-3,7-dimethylocta-2,6-dien-1-yl acetate); NONADYL (6,8-dimethylnonan-2-ol); NONENAL-6-CIS ((Z)-non-6-enal); NYMPHEAL™ (3-(4-isobutyl-2-methylphenyl)propana); ORIVONE™ (4-(tert-pentyl)cyclohexanone); PARADISAMIDE™ (2-ethyl-N-methyl-N-(m-tolyl)butanamide); PELARGENE (2-methyl-4-methylene-6-phenyltetrahydro-2H-pyran); PEONILE™ (2 cyclohexylidene-2-phenylacetonitrile); PETALIA™ (2-cyclohexylidene-2-(o-tolyl)acetonitrile); PIVAROSE™ (2,2-dimethyl-2-pheylethyl propanoate); PRECYCLEMONE™ B (1-methyl-4-(4-methylpent-3-en-1-yl)cyclohex-3-enecarbaldehyde); PYRALONE™ (6-(sec-butyl)quinoline); RADJANOL™ SUPER ((E)-2-ethyl-4-(2,2,3-trimethylcyclopent-3-en-1-yl)but-2-en-1-ol); RASPBERRY KETONE (N112) (4-(4-hydroxyphenyl)butan-2-one); RHUBAFURANE™ (2,2,5-trimethyl-5-pentylcyclopentanone); ROSACETOL (2,2,2-trichloro-1-phenylethyl acetate); ROSALVA (dec-9-en-1-ol); ROSYFOLIA ((1-methyl-2-(5-methylhex-4-en-2-yl) cyclopropyl)-methanol); ROSYRANE™ SUPER (4-methylene-2-phenyltetrahydro-2H-pyran); SERENOLIDE (2-(1-(3,3-dimethylcyclohexyl)ethoxy)-2-methylpropyl cyclopropanecarboxylate); SILVIAL™ (3(4 isobutylphenyl)-2-methylpropanal); SPIROGALBANONE™ (1-(spiro[4.5]dec-6-en-7-yl)pent-4-en-1-one); STEMONE™ ((E)-5-methylheptan-3-one oxime); SUPER MUGUET™ ((E)-6-ethyl-3-methyloct-6-en-1-ol); SYLKOLIDE™ ((E)-2-((3,5-dimethylhex-3-en-2-yl)oxy)-2-methylpropyl cyclopropanecarboxylate); TERPINENE GAMMA (1-methyl-4-propan-2-ylcyclohexa-1,4-diene); TERPINOLENE (1-methyl-4-(propan-2-ylidene)cyclohex-1-ene); TERPINYL ACETATE (2-(4-methylcyclohex-3-en-1-yl)propan-2-yl acetate); TETRAHYDRO LINALOOL (3,7-dimethyloctan-3-ol); TETRAHYDRO MYRCENOL (2,6-dimethyloctan-2-ol); THIBETOLIDE (oxacyclohexadecan-2-one); TRIDECENE-2-NITRILE ((E)-tridec-2-enenitrile); UNDECAVERTOL ((E)-4-methyldec-3-en-5-ol); VELOUTONE™ (2,2,5-trimethyl-5-pentylcyclopentanone); VIRIDINE™ ((22 dimethoxyethyl)benzene); ZINARINE™ (2-(2,4-dimethylcyclohexyl)pyridine); and mixtures thereof.

The perfume ingredients and cosmetic actives for use in the encapsulated compositions are preferably hydrophobic. Preferably, the cosmetic actives have a calculated octanol/water partition coefficient (C log P) of 1.5 or more, more preferably 3 or more. Preferably, the C log P of the cosmetic active is from 2 to 7.

Particularly useful cosmetic actives may be selected from the group consisting of emollients, smoothening actives, hydrating actives, soothing and relaxing actives, decorative actives, deodorants, anti-aging actives, draining actives, remodelling actives, skin levelling actives, preservatives, anti-oxidant actives, antibacterial or bacteriostatic actives, cleansing actives, lubricating actives, structuring actives, hair conditioning actives, whitening actives, texturing actives, softening actives, anti-dandruff actives, and exfoliating actives.

Particularly useful cosmetic actives include, but are not limited to, hydrophobic polymers, such as alkyldimethylsiloxanes, polymethylsilsesquioxanes, polyethylene, poly-isobutylene, styrene-ethylene-styrene and styrene-butylene-styrene block copolymers, and the like; mineral oils, such as hydrogenated isoparaffins, silicone oils and the like; vegetable oils, such as argan oil, jojoba oil, aloe vera oil, and the like; fatty acids and fatty alcohols and their esters; glycolipides; phospholipides; sphingolipides, such as ceramides; sterols and steroids; terpenes, sesquiterpenes, triterpenes and their derivatives; essential oils, such as *arnica* oil, *artemisia* oil, bark tree oil, birch leaf oil, calendula oil, cinnamon oil, *echinacea* oil, *eucalyptus* oil, *ginseng* oil, jujube oil, *helianthus* oil, jasmine oil, lavender oil, lotus seed oil, *perilla* oil, rosmary oil, sandal wood oil, tea tree oil, thyme oil, valerian oil, wormwood oil, ylang ylang oil, *yucca* oil and the like.

In an embodiment, the cosmetic active may be selected from the group consisting of sandal wood oil, such as fusanus spicatus kernel oil; panthenyl triacetate (CAS-No.: 94089-18-6); tocopheryl acetate; tocopherol, naringinin (CAS-No.: 480-41-1); ethyl linoleate; farnesyl acetate; farnesol; citronellyl methyl crotonate (CAS-No.: 20770-40-5); ceramide-2 (1-stearoiyl-C18-sphingosine, CAS-No: 100403-19-8); and mixtures thereof.

The functional core material may optionally be admixed with various hydrophobic excipients, such as apolar solvents, oils, waxes and apolar polymers.

A broad selection of shell-forming monomer, pre-polymers or pre-condensates can be used to form core-shell microcapsules of the present invention. These shell-forming materials may be selected from the group consiting of inorganic materials, such as silicate, metals and metal oxides, or organic materials, such as surfactants, natural, semi-synthetic and synthetic organic polymers, and mixture thereof. Particularly suitable are shells comprising silicates, gelatin, gelatin/gum *arabicum* complexes, gelatin/carboxymethyl cellulose complexes, alginate/calcium complexes, surfactant lamellar phases, and thermosetting resins, such as aminoplast resins, polyurea resins, polyurethane resins and polyacrylatre resins.

In a particular embodiment, the shell of the core-shell microcapsules comprises an aminoplast resin. Such microcapsules can be obtained by the steps of:
 a) dispersing droplets of functional material in an aqueous phase comprising an emulsifier in the presence of an amino-aldehyde pre-condensate;
 b) causing the monomers, pre-polymers or pre-condensates to react at the interface of the droplets and the aqueous phase to form a slurry of nascent core-shell microcapsules. The polycondensation is performed at a temperature of 85±10° C. for from about 1 to about 4 hours and at a pH of 3.9±1.0;
 c) adding a hyperbranched polymer to the slurry of nascent core-shell microcapsules to form a composition comprising a slurry of core-shell microcapsules, wherein the hyperbranched polymer is embedded into and/or attached onto the shells of the core-shell microcapsules;
 d) optionally adding to the slurry one more of a suspending agent, a preservative or any other conventional excipients;
 e) optionally dehydrating the slurry to form a composition of core-shell microcapsules in powder form.

The emulsifier is preferably a polymeric stabilizer selected from the group consisting of acrylic copolymers bearing sulfonate groups, such as those available commercially under the trade mark LUPASOL™ (ex. BASF), such as LUPASOL™ PA 140 or LUPASOL™ VFR; copolymers of acrylamide and acrylic acid, copolymers of alkyl acrylates and N-vinylpyrrolidone, such as those available under the trade mark LUVISKOL™ (e.g. LUVISKO™ K 15, K 30 or K 90 ex. BASF); sodium polycarboxylates (ex. Polyscience Inc.) or sodium poly(styrene sulfonate) (ex. Polyscience Inc.); vinyl and methyl vinyl ether-maleic anhydride copolymers (e.g. AGRIMER™ VEMA AN, ex. ISP), and ethylene, isobutylene or styrene-maleic anhydride copolymers (e.g. ZEMAC™); ampholytic co-polymer formed from a cationic monomer containing quaternary ammonium groups; and a monomer that can form anions, more particularly a monomer that is based on acrylic acid, methacrylic acid or a derivative thereof, such as a copolymer of acrylic acid or methacrylic acid, and acrylamidopropyl-trimethylammonium chloride (APTAC) or methacrylamidopropyl-trimethylammonium chloride (MAPTAC), a terpolymer formed from acrylic acid monomer, MAPTAC monomer and acrylamide monomer).

The amino-aldehyde pre-condensate may be a reaction product, such as a polymer or co-polymer of at least one amine, such as urea, thiourea, alkyl urea, 6-substituted-2,4-diamino-1,3,5-triazines such as benzoguanamine or glycoluril, and melamine; and at least one aldehyde, such us formaldehyde, acetaldehyde, glyoxal or glutaraldehyde. Suitable amino-aldehyde pre-condensates include but are not limited to partially methylated mono- and poly-methylol-1,3,5-triamino-2,4,6-triazine pre-condensates, such as those commercially available under the Trade Mark CYMEL™ (ex. Cytec Technology Corp.) or LURACOLL™ (ex. BASF), and/or mono- and polyalkylol-benzoguanamine pre-condensates, and/or mono- and polyalkylol-glycouril pre-condensates. These alkylolated polyamines may be provided in partially alkylated forms, obtained by addition of short chain alcohols having typically 1 to 6 methylene units.

In another particular embodiment, the shell of the core-shell microcapsules comprises a polyurea resin. Such microcapsules are obtained by the steps of:
 a) dispersing droplets of functional material in an aqueous phase comprising an emulsifier in the presence of a polyisocyanate;
 b) causing the monomers, pre-polymers or pre-condensates to react at the interface of the droplets and the aqueous phase to form a slurry of nascent core-shell microcapsules. The reaction is performed in the presence of a polyamine at a temperature of 80±5° C. for from about 2 to about 6 hours and at a pH of 8.5±1.0;
 c) adding a hyperbranched polymer to the slurry of nascent core-shell microcapsules to form a composition comprising a slurry of core-shell microcapsules, wherein the hyperbranched polymer is embedded into the shells of the core-shell microcapsules;
 d) optionally adding to the slurry one more of a suspending agent, a preservative or any other conventional excipients;
 e) optionally dehydrating the slurry to form a composition of core-shell microcapsules in powder form.

The polyisocyanates may be selected from the group consisting of 1,6-diisocyanatohexane (CAS No.: 822-06-0), 1,5-diisocyanato-2-methylpentane (CAS No.: 34813-62-2), 1,4-diisocyanato-2,3-dimethylbutane, 2-ethyl-1,4-diisocyanatobutane, 1,5-diisocyanatopentane (CAS No.: 4538-42-5), 1,4-diisocyanatobutane (CAS No.: 4538-37-8), 1,3-diisocyanatopropane (CAS NO.: 3753-93-3), 1,10-diisocyanatodecane (CAS No.: 538-39-0), 1,2-diisocyanatocyclobutane, bis(4-isocyanatocyclohexyl)methane (CAS No.: 5124-30-1), 3,3,5-trimethyl-5-isocyanatomethyl-1-isocyanatocyclohexane (CAS No.: 4098-71-9), 2-Imidodicarbonic diamide (CAS No.: 4035-89-6), biuret (CAS No.: 108-19-0), polyisocyanurate of toluene diisocyanate (CAS No.: 141-78-6, commercially available from Bayer under the Trade Name DESMODUR™ RC), trimethylol propane pre-condensate of polyisocyanurate of 1,6-diisocyanatohexane (CAS No.: 53200-31-0, commercially available from Bayer under the Trade Name DESMODUR™ N100), trimethylol propane pre-condensate of toluene diisocyanate (CAS No.: 9081-90-7, commercially available from Bayer under the Trade Name DESMODUR L75), trimethylol propane pre-condensate of xylylene diisocyanate (CAS No.: 865621-91-6; commercially available from Mitsui Chemicals under the Trade Name TAKENATE D-110N). Also included are modified isocyanates, such as aliphatic polyisocyanate based on hexamethylene diisocyanate and alkylene oxide, especially ethylene oxide, (sold under the name BAYHYDUR™), for example Bayhydur™ XP 2547 (commercially available from Bayer); and mixtures thereof. Polyamines may be selected from the group consisting of 1,2-ethylenediamine, 1,3-diaminopropane, 1,4-diaminobutane, 1,6-diaminohexane, hydrazine; 1,4-diaminocyciohexane, 1,3-diamino-1-methylpropane, diethylenetriamine, triethylenetetramine, bis(2-methylaminoethyl)ether (CAS No.: 3033-62-3), guanidine (CAS No.: 113-00-8), guanidine carbonate salt (CAS No 593-85-1), 3,5-diamino-1,2,4-triazole (CAS No.: 1455-77-2), melamine, urea, polymeric polyamines such as poly (vinylamine), such as those available commercially under the trade name LUPAMINE™ (ex. BASF), poly(ethyleneimine) (CAS No.: 9002-98-6)), such as those available commercially under the trade name LUPASOL™ (ex. BASF); poly(etheramine), such as those available commercially under the trade name JEFFAMINE™ (ex. Huntsman); and mixtures thereof.

The emulsifier is preferably a polymeric stabilizer selected from the group consisting of maleic/vinyl copolymers, sodium lignosulfonates, maleic anhydride/styrene copolymers, ethylene/maleic anhydride copolymers, and copolymers of propylene oxide, ethylenediamine and ethylene oxide, polyvinylpyrrolidone, polyvinyl alcohols, fatty acid esters of polyoxyethylenated sorbitol and sodium dodecylsulfate. Polyvinylpyrrolidone and polyvinyl alcohols are the G-polymer type, having a degree of hydrolysis in the range of 85 to 99.9%, available under the trade name GOSHENOL™ from Nippon Gohsei Nichigo.

In carrying out step c) the addition of hyperbranched polymer may be made before the shell-forming monomer, pre-polymers or pre-condensates are caused to react, or during the reaction of these materials. The entire amount of hyperbranched polymer may be added in one operation, or it can be added sequentially and/or portion wise.

The amount of hyperbranched polymer added may vary within wide limits, and more particularly it may be added in an amount of about 0.01 to about 1 wt %, more particularly from about 0.02 to about 0.5 wt % and still more particularly from 0.05 to 0.25 wt %, based on the total weight of of the system (i.e. the emulsion in case the hyperbranched polymer is added before the encapsulation takes place or the slurry in case the hyperbranched polymer is added during or after encapsulation).

The extent of incorporation of hyperbranched polymer in or on the microcapsule shell may be obtained by subtracting the amount of free hyperbranched polymer present in the slurry after the coating process has been completed from the nominal amount of hyperbranched polymer initially added to the system.

A considerable advantage of hyperbranched polymers compared to linear polymers that are conventionally used as deposition aids resides is their low thickening potential, which allows them to be used at much higher levels in microcapsule slurries without inducing high viscosity issues. This results in higher incorporation of hyperbranched polymer in or on the microcapsule shell.

The level of free hyperbranched polysaccharides present in the slurry may be determined by using the method of Alabamesh (A. Albalasmeh et al., Carbohyd, Poly. 2013, 97, 253-261), based on Dubois colorimetric determination of carbohydrates (M. Dubois et al., Anal. Chem. 1956, 28, 350-356). The method involves separating the microcapsules from the aqueous phase of the slurry by centrifugation, adding concentrated sulfuric acid to the the diluted supernatant and measuring the UV/VIS absorbance at a wavelength of 350 nm. A detailed procedure is given in Example 2.

Typically, from 40 to 99%, more particularly from 50 to 80% and still more particularly from 55 to 70% of the added hyperbranched polymer is effectively embedded into and/or attached onto the microcapsule shells.

Although adding to the slurry one more of a suspending agent, a preservative or any other conventional excipients is optional, it is conventional to stabilize a slurry by adding certain well-known excipients.

For example, once the slurry is formed, one can add a suspending agent to it in order to prevent the slurry from phase-separating, such as creaming or sedimenting. Any of the conventional suspending agents may be employed in the present invention. Coventional suspending agents include but are not limited to a hydrocolloid selected from the group consisting of starch and starch derivatives, such as modified starch, dextrin, maltodextrin; gums, such as gum arabic or gum accacia, xanthan gum, gum tragacanth, gum karaya, guar gum; cellulose and cellulose derivatives, such as carboxy methyl cellulose, hydroxyethyl cellulose, hydroxyethyl cellulose/lauryl-dimethylammoniumepoxy condensat, hydroxypopyl cellulose, cationic cellulose (for example polyquaternium-4), cellulose gum; carrageenan; agar-agar; pectines and pectic acid; gelatine; protein hydrolysates; polymer and copolymers of vinyl and allyl monomers, such as polyvinylpyrrolidone; poly(vinyl pyrrolidone-co-vinylacetate); poly(vinyl alcohol-co-vinyl acetate) (more particularly hydrolyzed polyvinylacetates having a degree of hydrolysis between 85 and 92%), vinyl ester homopolymers and copolymers, such as vinyl acetate, vinyl pivalate, vinyl versatate; poly(vinyl methyl ether), poly(vinyl alkyl amines), such as poylvinylmethylamine, quaternized polyvinyl alkyl amines, vinyl pyridine and quaternized vinyl pyridine, vinyl imidazoline, vinyl imidazole, vinyl imidazolinium, dimethyldiallyl ammonium chloride, vinyl sulphonate homopolymers and/or copolymers, polyamines and polyimines, ethoxylated polyamines, polymers, copolymers and cross-polymers derived from (meth)acryloyl monomers, such as methyl methyl acrylate, ethyl methacrylate, 2-ethylhexyl acrylate, lauryl methacrylate, C10-C30 alkyl acrylate, hydroxyalkyl (meth)acrylate, such as 2-hydroxypropyl acrylate and 2-hydroxypropyl methacrylate, acrylamidodimethyl taurate; aryl (meth)acrylates, such as phenyl acrylate and benzyl acrylate, (meth)acrylic acids and their salts, such as sodium and potassium (meth)acrylates, sodium acryloyldimethyltaurate; (meth)acrylamides; N-alkyl (meth)acrylamides, such as N,N-dimethylaminoalkyl methacrylate; quaternized N-alkyl (meth)acrylamides, such as methacrylamidopropyl-trimethylammonium chloride; acrylamidoe-thyltrimonium chloride; acrylamidolauryltrimethylammonium chloride; and (meth)acrylamido alkyl sulphonates poly(male ic anhydride) and poly(maleic anhydride-co-vinyl ether), and their hydrolysates; poly(acrylic acid-co-maleic acid)copolymer, poly(alkyleneoxide), polyurethanes and polyureas, such as anionic, cationic non-ionic and amphoteric polyurethanes and polyureas; mixed copolymers thereof; and mixture thereof.

It is also conventional to add biological preservatives to aqueous slurries to prevent unwanted growth of moulds and other microorganisms.

Suitable preservatives include, but are no limited to quaternary compounds, biguanide compounds (CAS No.: 32289-58-0, 27083-27-8, 28757-47-3, 133029-32-0), poylaminopropyl biguanidine, hexetidine, para-chloro-metacresol, methenamine, 3-bis(hydroxymethyl)-5,5-dimethylimidazolidine-2,4-dione, quaternium-15, benzoic acid, salicylic acid, undec-10-enoic acid, formic acid, biphenyl-2-ol and their salts, 4-hydroxybenzoic acid and its esters and salts; sorbic acid and its salts, isothiazolinones, 2-bromo-2-nitro-1,3-propanediol, 5-bromo-5-nitro-1,3-dioxane, 2-(thiazol-4-yl) benzimidazole, benzimidazole carbamate, 3-(4-ohlorophenyl)-1-(3,4-dichlorophenyl)uree, 3-iodo-2-propynylbutylcarbamate, ethyl(2-mercaptobenzoato-(2-)-O, S) mercurate(1-) sodium, 5-choro-2-(2,4-dichlorophenoxy) phenol, dichlorobenzyl alcohol, chloroxylenol, imidazolidinyl urea, phenoxyethanol, benzyl alcohol and mixtures thereof.

Compositions in the form of a slurry of core-shell microcapsules can be incorporated into all manner of consumer products. However, for some applications it might be desirable to add the core-shell microcapsules in the form of a dry powder. Thus, in accordance with the present invention, in an optional step for dehydrating the slurry to form a composition of core-shell microcapsules in powder form, the slurry may be dehydrated to provide the composition of the present invention in dry powder form.

If desired, the microcapsules can be isolated in the form of a dry powder. For example, the solid capsules can be isolated by filtration and dried. Drying of the isolated capsules may be performed by heating, e.g. in an oven or by contact with a heated gas stream. Preferably, drying of the dispersion is carried out by spray drying or fluid-bed drying. Spray drying techniques and apparatus are well known in the art. A spray-drying process pushes suspended capsules through a nozzle and into a drying chamber. The capsules may be entrained in a fluid (such as air) that moves inside of a drying chamber. The fluid (which may be heated, for example at a temperature of 150 and 120° C., more preferably between 170° C. and 200° C., and still more preferably between 175° C. and 185° C.) causes the liquid to evaporate, leaving behind the dried capsules which can then be collected from the process equipment and further processed.

Prior to or after the spray drying step, it may be desirable to add a flow aid, such as silica or the like to the slurry to ensure the realization of fine, free-flowing powdered microcapsules with low surface perfume oil. Flow aids include silicas or silicates, such as precipitated, fumed or colloidal silicas, starches, calcium carbonate, sodium sulphate, modified cellulose, zeolites or other inorganic particulates known in the art.

The slurry of microcapsules may be spray-dried in a conventional spray drying tower, using a two-fluid nozzle or spin-dried in a conventional spin dryer. If desired, at least one hydrocolloid may be added to the microcapsule slurry, as such or in the form of an aqueous solution. Typical hydrocolloids include starch, modified starch such as dextrin-modified with octenyl succinate anhydride, and gum arabic. Optionally, maltodextrins and sugar alcohols, such as sorbitol, mannitol or maltitol may also be added. The hydrocolloid may itself contain a functional material. This functional material may be the same as, or different form, that the core material in the capsule. This is achieved by performing the step of (1) emulsifying a second functional material in aqueous hydrocolloid solution, optionally comprising maltodextrins and sugars or sugar alcohols to form a second slurry (2) mixing the second slurry with a slurry of microcapsules comprising a first functional material and (3) drying this mixture. Such a process is described in WO 2007/137441 A1, Example 5.

By means of the present invention it is possible to obtain compositions in the form of a slurry of core-shell microcapsules that have a high core content, typically within the range of 30 to 50 wt %, and more particularly from 35 to 45 wt %.

Still further, the core-shell microcapsules may have a volume-average diameter from 0.5 to 25 micrometres, more particularly from 1 to 20 micrometres, still more particularly from 5 to 15 micrometres, for example 10±2 micrometres.

Microcapsule size can be determined in a manner known in the art. A particular method of measuring particle size is light scattering. Light scattering measurements can be made using a Malvern Mastersizer 2000S instrument and the Mie scattering theory. The principle of the Mie theory and how light scattering can be used to measure droplet size can be found, for example H. C. van de Hulst, Light scattering by small particles. Dover, N.Y., 1981. The primary information provided by static light scattering is the angular dependence of the light scattering intensity, which in turn is linked to the size and shape of the droplets. However, in a standard operation method, the size of a sphere having a size equivalent to the size of the diffracting object, whatever the shape of this object, is calculated by the Malvern proprietary software provided with the apparatus. In case of polydisperse samples, the angular dependence of the overall scattering intensity contains information about the size distribution in the sample. The output is a histogram representing the total volume of droplets belonging to a given size class as a function of the capsule size, whereas an arbitrary number of 50 size classes can be chosen. Thus, the size obtained is referred to as volume-average particle size.

Experimentally, a few drops of slurry are added to a circulating stream of degassed water flowing through a scattering cell. The angular distribution of the scattering intensity is measured and analysed by Malvern proprietary software to provide the average size and size-distribution of the droplets present in the sample. In the case of an unimodal (monodisperse) droplet distribution the percentiles Dv(10), Dv(50) and Dv(90) are used as characteristics of the droplets size distribution, whereas Dv(50) corresponds to the median of the distribution and is taken as a measure of the volume-average size of the microcapsules. The compositions according to the present invention may be incorporated into all manner of consumer products.

Typical consumer products concerned by the present invention include personal care cleaning and cleansing compositions, such as shampoos, bath and shower gels, liquid soaps, soap bars and the like, laundry care products, such as detergents, and home care products, such as hard surface cleaners.

In many cases, the consumer products concerned by the present invention contain surfactants, such as anionic, cationic, amphoteric or non-ionic surfactants.

In a preferred embodiment of the present invention, the consumer product comprising a composition as stated hereinaboveis a shampoo comprising anionic surfactants, non-ionic surfactants, water-soluble solvents, one or more preservative, and optionally benefit agents that may be selected from the group consisting of moisturizers, emollients, thickeners, anti-dandruff agents, hair growth promoting agents, vitamins, nutrients, dyes, hair colorants, and the like.

Typical formulation ingredients for use in shampoo with our without microcapsules may be found, for example, in EP 0 191 564 A2 or WO 1997/023194 A1.

The microcapsules are preferably at a level of about 0.01 to 5 wt %, more particularly from about 0.1 to 2.5 wt % and still more particularly from about 0.2 to 1 wt % of the personal care product, referred to the total weight of the shampoo composition.

In another embodiment of the present invention, the consumer product comprising core-shell microcapsules is a liquid soap comprising one or more anionic surfactant, and other surfactants that may be selected from the group consisting of mixtures of fatty acids and neutralized fatty acids, aminoxide surfactants, non-ionic surfactants, zwitterionic surfactants, and mixtures thereof; electrolytes; one or more preservative; and optionally benefit agents that may be selected from the group consisting of pH-control agents, skin care agents, moisturizers, emollients, thickeners, vitamins, nutrients and dyes.

Typical formulation ingredients for use in liquid soaps may be found, for example, in CA 2812137 A1 or US2003/0050200 A1.

The core-shell microcapsules are preferably at a level of about 0.01 to 5 wt %, more particularly from about 0.1 to 2.5 wt % and still more particularly from about 0.2 to 1 wt % of the personal care product, referred to the total weight of the liquid soap composition.

In another embodiment of the present invention, the consumer product comprising core-shell microcapsules is a shower gel comprising one or more anionic surfactant, and other surfactants that may be selected from the group consisting of mixtures of fatty acids and neutralized fatty acids, aminoxide surfactants, non-ionic surfactants, zwitterionic surfactants, aminoxide surfactants, aminoxide surfactants, and mixture thereof; electrolytes, such one or more preservative; and optionally benefit agents that may be selected from the group consisting of thickeners, pH-control agents; skin care agents, moisturizers, emollients, thickeners, vitamins, nutrients, dyes, and the like.

Typical formulation ingredients for use in shower gels may be found, for example, in U.S. Pat. No. 5,607,678 or US 2012/0263668 A1.

The core-shell microcapsules are preferably at a level of about 0.01 to 5 wt %, more particularly from about 0.1 to 2.5 wt % and still more particularly from about 0.2 to 1 wt % of the personal care product, referred to the total weight of the shower gel composition.

Once deposited on the keratinous surfaces, the core-shell microcapsules are able to release their functional material by diffusion through the microcapsule shell or following the mechanical rupture of the microcapsule shell. Mechanical rupture may follow a mechanical action, such as rubbing, squeezing, combing, washing and the like or heating, for example using a hair dryer.

Diffusion-mediated release is particularly desired if the functional material is a fragrance composition, because, in this case, a nice smell may be perceived over a long time, for example several hours, after application of the microcapsules on the substrate. On the other hand a mechanical rupture may provoke a surprising and pleasant boost of odor.

Further advantages and particular features of the present invention become apparent from FIG. 1 and from the following discussion of several examples.

FIG. 1 illustrates the deposition and rinse resistance for shampoo and hair care conditioner compositions obtained in Example 3.

EXAMPLE 1

Preparation of aminoplast core-shell microcapsules comprising a hyperbranched polymer embedded in the shell of the core-shell microcapsules and a fragrance as core material.

The microcapsules were prepared by performing the steps of:
a) Preparing an aqueous solution containing 72 g of emulsifier LUPASOL™ PA 140 (ex. BASF, 20% active, effective amount of active: 14 g), 19 g of resin precursor LURACOLL™ SD (ex. BASF, 70% active, effective amount or active: 13.3 g) and 6.7 g resorcinol and 324 g water;
b) emulsifying 355 g fragrance to the aqueous solution obtained in step a) by mixing at a stirring speed of 1000 rpm, using a a cross-beam stirrer with pitched bean;
c) adjusting the pH of the emulsion obtained in a) to a value of 3.5±0.3 by adding 11.1 g of 10% formic acid and heating the emulsion to 90° C.;
d) maintaining the temperature at 90° C. over a period of one hour under agitation, to form thermosetting aminoplast resin wall around the droplets, thereby forming a slurry of microcapsules having a diameter of 10 micrometres (µm);
e) adding a defined amount of selected hyperbranched polysaccharide solution at 2 wt % in water (as specified hereunder);
f) adding 11.1 g of 10% formic acid and 11.1 g of resin precursor LURACOLL™ SD (ex. BASF, 70% active, effective amount or active: 7.8 g), while maintaining the temperature at 90° C. for an additional 2 hours;
g) cooling down the slurry to room temperature and adding 3.2 g of 10% solution of ammoniac in water to obtain a pH between 5.5 and 7.

The defined amounts of hyperbranched polysaccharide solution at 2 wt % in water were 50 g of solution (corresponding to 0.1 wt % of hyperbranched polysaccharide in slurry) and 150 g of solution (corresponding to 0.3 wt % of hyperbranched polysaccharide in slurry). The hyperbranched polsaccharide was amylopectin.

The solid content of the slurry was measured by using a thermo-balance operating at 120° C. The solid content, expressed as weight percentage of the initial slurry deposited on the balance was taken at the point where the drying-induced rate of weight change had dropped below 0.1%/min. The solid content of the slurry was 42±1 wt %. A comparative example without hyperbranched polymer is obtained by substantially the same process as described above, but with the omission of the hyperbranched polymer addition step f).

EXAMPLE 2

Determination of free polysaccharide in slurries prepared according to Example 1.

The level of free polysaccharide is determined by performing the steps of:
a) diluting the slurry to obtain a solid content of about 10 wt % (dilution factor 4);
b) centrifuging the diluted slurry for 30 minutes at 3000 rpm;
c) sampling the supernatant with a syringe and ultracentrifuging this supernatant for 30 minutes at 13000 rpm;

d) sampling again the supernatant and filtering this supernatant through a microporous filter;
e) admixing 3 ml of filtered supernatant diluted 10 times in deionized water with 7 ml of concentrated sulfuric acid at 98 vol % (as supplied by Sigma Aldrich);
f) cooling down the mixture and completing to 10 ml with deionized water;
g) measuring the absorbance at a wavelength of 350 nm and comparing the absorbance value to those of a calibration curve obtained from standard hyperbranched polymer solutions.

The levels of free hyperbranched polymer in the different samples are reported in Table 1 below.

The level of hyperbranched polymer embedded in the shell of the core-shell microcapsules is obtained by subtracting the level of free hyperbranched polymer from the total level of hyperbranched polymer added to the slurry.

EXAMPLE 3

Preparation of shampoo and hair care conditioner compositions and deposition data.

The microcapsule slurries of Example 1 were added to a shampoo composition under gentle stirring with a paddle mixer, so that the level of slurry in the shampoo base was 0.5 wt % referred to the total weight of the shampoo base. The mixture was let to macerate overnight before performing the deposition measurements. 4.8 g of base was applied on 48 g hair swatches by rubbing over 20 seconds. The swatches were then let to rest for 1 minute and then rinsed 30 seconds under running tap water at 37° C. at a flow rate of 3.2 l/min, without touching the swatch by hand.

The deposition values were obtained by image analysis micrographs obtained with a fluorescence light microscope at a magnification of 40×, using Stream Motion software and Hostasol Yellow 3G as fluorescent agent at 0.02 wt % in perfume, 450 nm excitation wavelength and 500 nm emission wavelength.

In the case of hair conditioner, the microcapsule slurries of Example 1 were added to a hair care conditioner composition under gentle stirring with a paddle mixer, so that the level of slurry in the hair care conditioner base was 1 wt % referred to the total weight of the hair care conditioner base. 1.5 g of hair care conditioner was applied on 15 g swatches humidified with 12 g water. The swatches were submitted to a massage, left to stand for 1 minute and then rinse rinsed 30 seconds under running tap water at 37° C. at a flow rate of 3.2 l/min, without touching the swatch by hand.

The deposition values were determined as described herein above for the case of shampoo.

The compositions of the model shampoo and hair care conditioner bases are given in Table 2 and 3.

TABLE 1

Results for shampoo

| Sample | Polymer | Total polymer level in slurry [%] | Level of free polymer [%] | Polymer embedded in the shell [%] | Deposition [# capsules/mm²] |
|---|---|---|---|---|---|
| 1 | None | | | | 0.3 ± 0.1 |
| 2 | Linear hemicellulose | 0.3 | 0.17 | 0.13 | 0.9 ± 0.1 |
| 3 | Amylopectin | 0.1 | 0.035 | 0.065 | 1.8 ± 0.4 |
| 4 | Amylopectin | 0.3 | 0.12 | 0.18 | 1.7 ± 0.2 |

TABLE 2

Results for for hair care conditioner

| Sample | Polymer | Total polymer level in slurry [%] | Level of free polymer [%] | Polymer embedded in the shell [%] | Deposition [# capsules/mm²] |
|---|---|---|---|---|---|
| 1 | None | | | | 0.3 ± 0.2 |
| 2 | Linear hemicellulose | 0.3 | 0.17 | 0.13 | 2 ± 0.9 |
| 3 | Amylopectin | 0.1 | 0.035 | 0.065 | 4.5 ± 1.6 |
| 4 | Amylopectin | 0.3 | 0.12 | 0.18 | 4.7 ± 1.6 |

The results of Tables 1 and 2 are illustrated in FIG. 1. They confirm that core-shell microcapsules with a shell comprising a hyperbranched polymer show an enhanced deposition and rinse resitance on hair from both shampoo and conditioner compositions, compared to situations where no polymer or a linear polymer is used.

TABLE 3

Model shampoo base composition

| Ingredient trade name | INCI name | Percentage by weight in shampoo |
|---|---|---|
| PROPYLENE GLYCOL | Propylene Glycol | 1.00 |
| JAGUAR ™ C-13S (ex. RHODIA) | Guar Hydroxypropyltrimonium Chloride | 0.25 |
| MARLINAT ™ 242/28 (ex. SASOL) | Sodium Laureth Sulfate | 25.00 |
| DEHYTON ™ AB 30 (ex. COGNIS) | Coco Betaine | 5.00 |
| EUPERLAN ™ PK 3000 (ex. COGNIS) | Glycol distearate, Laureth-4 and Cocoamidopropyl Betaine | 0.50 |
| GLYDANT ™ PLUS LIQ (ex. LONZA) | DMDM Hydantoin | 0.50 |
| SODIUM CHLORIDE | Sodium Chloride | 1.20 |
| BC 2102 (ex. BALLU CHIMIE) | Dimethiconol Emulsion | 2.00 |
| DEIONIZED WATER | | QSP 100 |

TABLE 4

Model hair conditioner base composition

| Ingredient trade name | INCI name | Percentage by weight in conditioner |
|---|---|---|
| PHENONIP ™ (ex. CLARIAN) | Phenoxyethanol and Butyl and Ethyl and Propyl parabens | 0.70 |
| BRIJ ™ 721 (ex. UNIQEMA/MASSO) | Steareth-21 | 2.00 |
| LANETTE ™ 16 (ex. COGNIS) | Cetyl alcohol | 1.00 |
| PROPYLENE GLYCOL (ex. PRODH'YG) | Propylene glycol | 4.00 |
| NATROSOL ™ 250H (ex. AQUALON) | Hydroxyethylcellulose | 0.90 |
| INCROQUAT ™ CTC 30 (ex. CRODA) | Cetrimonium chloride | 2.00 |
| DEIONIZED WATER | | QSP 1100 |

The invention claimed is:

1. A composition comprising at least one core-shell microcapsule in a suspending medium for deposition on a keratinous substrate, wherein said microcapsule comprises a core and a shell around said core, wherein said shell comprises a hyperbranched polysaccharide selected from the group consisting of amylopectins, dextrins, hyperbranched starches, glycogen, phytoglycogen and mixtures thereof, wherein the amount of hyperbranched polysaccharide is from 0.01 to 1 wt %, referred to the total weight of the microcapsule suspension and wherein said hyperbranched polysaccharide is embedded into the microcapsule shell.

2. The composition according to claim 1, wherein the ratio of 1,6'-glycosidic bonds to 1,4'-glycosidic bonds in said hyperbranched polysaccharide is greater than 1/50.

3. The composition according to claim 1, wherein said core comprises an ingredient selected from the group consisting of a fragrance ingredient, a cosmetic ingredient and a mixture thereof.

4. The composition according to claim 1, wherein said shell of said at least one core-shell microcapsule comprises a thermosetting resin.

5. A method of embedding hyperbranched polysaccharide into microcapsule shells, said method comprising the steps of:
dispersing droplets of a core material in a suspending medium in the presence of a shell-precursor selected from the group consisting of shell-forming monomers, pre-polymers and pre-condensates, to obtain an emulsion;
causing said shell-forming monomers, pre-polymers or pre-condensates to react at the interface of the droplets and the suspending medium to obtain a slurry of core-shell microcapsules;
adding a hyperbranched polysaccharide to the slurry of core-shell microcapsule, thereby obtaining a composition comprising core-shell microcapsules in a suspending medium for deposition on a keratinous substrate, wherein said hyperbranched polysaccharide is embedded into the shells of said core-shell microcapsules;
wherein the hyperbranched polysaccharide is selected from the group consisting of amylopectins, dextrins, hyperbranched starches, glycogen, phytoglycogen and mixtures thereof, and
wherein the amount of hyperbranched polysaccharide is from 0.01 to 1 wt %, referred to the total weight of the microcapsule suspension.

6. A method for increasing rinse-resistance of at least one core-shell microcapsule deposited on a keratinous surface, the method comprising the step of embedding a hyperbranched polysaccharide into the shell of the core-shell microcapsule,
wherein said microcapsule comprises a core and a shell around said core, wherein the core-shell microcapsule is in a suspending medium for deposition on the keratinous surface, wherein the hyperbranched polysaccharide is selected from the group consisting of amylopectins, dextrins, hyperbranched starches, glycogen, phytoglycogen and mixtures thereof, and wherein the amount of hyperbranched polysaccharide is from 0.01 to 1 wt %, referred to the total weight of the microcapsule suspension.

7. A consumer product comprising a composition according to claim 1.

8. The consumer product according to claim 7, wherein said consumer product is selected from the group consisting of a shampoo, a hair care conditioner, a shower gel and a liquid soap.

9. The composition according to claim 2, wherein the ratio of 1,6'-glycosidic bonds to 1,4'-glycosidic bonds in said hyperbranched polysaccharide is greater than 1/40.

10. The composition according to claim 9, wherein the ratio of 1,6'glycosidic bonds to 1,4'-glycosidic bonds in said hyperbranched polysaccharide is greater than 1/35.

11. The composition according to claim 1, wherein the amount of hyperbranched polysaccharide is from 0.02 to 0.5 wt %, referred to the total weight of the microcapsule suspension.

12. The composition according to claim 11, wherein the amount of hyperbranched polysaccharide is from 0.05 to 0.25 wt %, referred to the total weight of the microcapsule suspension.

13. The composition according to claim 4, wherein the shell of said at least one core-shell microcapsule comprises a thermosetting resin selected from the group consisting of aminoplast resins, polyurea resins, polyacrylic resins and mixtures thereof.

14. The method according to claim 5, additionally comprising the step of adding to said slurry one or more of a suspending agent or a preservative.

15. The method according to claim 5, additionally comprising the step of dehydrating said slurry to form a composition of core-shell microcapsules in powder form.

16. The composition of claim 1 which is a keratinous substrate treatment composition.

* * * * *